(12) United States Patent
Hell et al.

(10) Patent No.: US 7,863,585 B2
(45) Date of Patent: Jan. 4, 2011

(54) STED-FLUORESCENT LIGHT MICROSCOPY WITH TWO-PHOTON EXCITATION

(75) Inventors: Stefan W. Hell, Göttingen (DE); Katrin Willig, Göttingen (DE)

(73) Assignee: Max-Planck-Gesellschaft zur Förderung der Wissenschaften e.V., München (DE)

( * ) Notice: Subject to any disclaimer, the term of this patent is extended or adjusted under 35 U.S.C. 154(b) by 0 days.

(21) Appl. No.: 12/706,388

(22) Filed: Feb. 16, 2010

(65) Prior Publication Data
US 2010/0176307 A1 Jul. 15, 2010

Related U.S. Application Data

(63) Continuation of application No. PCT/EP2008/060694, filed on Aug. 14, 2008.

(51) Int. Cl.
*G01N 21/64* (2006.01)
(52) U.S. Cl. ............................... 250/459.1; 250/458.1
(58) Field of Classification Search ............... 250/234, 250/339.01, 458.1, 459.1, 461.2, 492.2; 356/300, 318
See application file for complete search history.

(56) References Cited

U.S. PATENT DOCUMENTS

| | | | | |
|---|---|---|---|---|
| 5,952,668 | A * | 9/1999 | Baer | 250/492.2 |
| 6,483,735 | B1 * | 11/2002 | Rentzepis | 365/119 |
| 6,958,470 | B2 | 10/2005 | Hoffmann | |
| 2001/0045523 | A1 | 11/2001 | Baer | |
| 2002/0104961 | A1 | 8/2002 | Hoffman | |
| 2005/0122579 | A1 * | 6/2005 | Sasaki | 359/385 |
| 2006/0187533 | A1 * | 8/2006 | Nielsen et al. | 359/333 |

(Continued)

FOREIGN PATENT DOCUMENTS

DE 10 2005 027 896 A1 12/2006

(Continued)

OTHER PUBLICATIONS

Donnert G. et al.: "Macromolecular-scale resolution in biological fluorescence microscopy" Proc. Nat. Acad. Sci., vol. 103, No. 31, Aug. 1, 2006, pp. 11440-11445.

(Continued)

*Primary Examiner*—David P Porta
*Assistant Examiner*—Marcus H Taningco
(74) *Attorney, Agent, or Firm*—Thomas, Kayden, Hordtemever & Risley, LLP

(57) ABSTRACT

A method of high spatial resolution imaging a structure in a sample comprises: marking the structure with molecules of a fluorescent dye; selecting a first wavelength for excitation light which excites the molecules of the fluorescent dye via a multi photon process for spontaneous emission of fluorescent light; focusing pulses of the excitation light into the sample to excite those molecules of the fluorescent dye present in a focal area of the focused excitation light; selecting a second wavelength shorter than the first wavelength for de-excitation light which de-excites excited molecules of the fluorescent dye prior to their spontaneous emission; during a plurality of the pulses of the excitation light, continuously directing the de-excitation light onto the sample to de-excite excited molecules of the fluorescent dye, which are located outside an measurement area which is a fraction of the focal area; and recording the fluorescent light spontaneously emitted by the molecules of the fluorescent dye in the sample.

30 Claims, 1 Drawing Sheet

U.S. PATENT DOCUMENTS

2006/0290924 A1  12/2006  Iketaki et al.
2008/0088839 A1  4/2008  Hell et al.

FOREIGN PATENT DOCUMENTS

WO  91/07651  5/1991
WO  2007/030835 A2  3/2007

OTHER PUBLICATIONS

Dyba M et al.: "Phase filter enhanced STED-4Pi fluorescence microscopy: theory and experiment" New J. Phys., vol. 7, May 25, 2005, pp. 134-1-134-21.

English Translation of International Preliminary Report on Patentability and Search Report for co-pending, related PCT Application No. PCT/EP2008/060694, mailed Mar. 2, 2010.

* cited by examiner

STED-FLUORESCENT LIGHT MICROSCOPY WITH TWO-PHOTON EXCITATION

CROSS REFERENCE TO RELATED APPLICATIONS

The present application is a continuation of International Application PCT/EP2008/060694 entitled "STED-Fluorescence Microscopy having two-Photon Excitation", filed Aug. 14, 2008, and claims priority to co-pending German Patent Application No. DE 10 2007 039 111.2 entitled "STED-Fluoreszenzmikroskopie mit Zweiphotonen-Anregung", filed Aug. 18, 2007.

FIELD OF THE INVENTION

The invention relates to a method of high spatial resolution imaging a structure of interest in a sample, which is marked with molecules of a fluorescent dye, and to a high spatial resolution imaging system comprising a sample in which a structure of interest is marked with molecules of fluorescent dye. More particular, the present invention relates to a method and a system of STED (Stimulated Emission Depletion)-fluorescent light microscopy.

BACKGROUND OF THE INVENTION

In STED-fluorescent light microscopy, the diffraction barrier which normally is the resolution limit in far field light microscopy may be overcome. To this end, the diffraction limited focal area in which the excitation light generally excites the fluorescent dye in the sample for spontaneous emission of fluorescent light is reduced in size to dimensions below the diffraction barrier in that parts of the focal area are superimposed with de-excitation light which de-excites the excited fluorescent dye prior to its emission of fluorescent light. Thus, the fluorescent light spontaneously emitted by the fluorescent dye only originates from a measurement area which is reduced in size with regard to the focal area. By means of recording this spontaneously emitted fluorescent light, the structure of interest in the sample marked with the fluorescent dye is imaged at a spatial resolution surpassing the diffraction barrier. The achieved spatial resolution is particularly high, if the de-excitation light is directed onto the sample in the form of an interference pattern which has a null at the location of the measurement area and which otherwise exceeds a saturation threshold above which essentially every molecule of the fluorescent dye previously excited by the excitation light is de-excited by the de-excitation light.

A method and a system of STED fluorescent light microscopy are known from U.S. Pat. No. 5,731,588. In this patent, it is mentioned that the excitation light source may be a continuous wave laser (cw laser), whereas the de-excitation light source may be a pulse laser which is synchronized with the detector to record the fluorescent light from the sample only after the decay of each pulse of the de-excitation light. In this way, it is avoided that the detector collects de-excitation light reflected by the sample or even fluorescent light which was stimulated by the de-excitation light and thus does not originate from the measurement area of interest. As an alternative for extracting the spontaneously emitted fluorescent light, a polarization of the excitation light and polarization filtering the light getting from the sample onto the detector in a direction orthogonal to the polarization of the excitation light are described.

A means to achieve the desired saturation in de-exciting the fluorescent dye outside the measurement area after each pulse of the excitation light in STED fluorescent light microscopy is to concentrate the mean light intensity which is available for the de-excitation light in pulses which are applied to the sample as close in time as possible to the pulses of the excitation light to offer as little chances as possible to the fluorescent dye outside the measurement area to spontaneously emit fluorescent light. This proximity in time may be achieved by an immediate succession or by a partial or even by a complete overlap in time. However, an exact synchronization of the pulses of the de-excitation light with the pulses of the excitation light, in addition to the synchronization of the detector with the pulses of the de-excitation light, if required, is a precondition for this timing.

Thus, the efforts for realising an STED fluorescent light microscope or for upgrading a common fluorescent light microscope for STED fluorescent light microscopy are high, because synchronisable pulse lasers for the excitation light and for the de-excitation light are expensive. In addition, the laser pulses emitted by usual pulse lasers do not display a sufficient pulse duration for STED fluorescence microscopy. Besides the synchronization requirements, the necessary lengthening and preparation of the pulses via dispersive optical elements like grates and glass fibre arrangements result in high technical efforts and financial investments as well as in a susceptibility to functional failures.

In the field of cw lasers, less expensive lasers are generally available, like, for example, as so-called diode lasers which comprise one or more electrically pumped laser diodes. Pulse preparation and synchronization are omitted with cw lasers. If diode lasers are modified for the emission of single pulses, however, the technical and financial advantages generally provided by them get lost.

In the known forms of STED fluorescent light microscopy it turns out to be difficult to delimit the measurement area along the optical axis, because with a single photon excitation of the fluorescent dye, it is in principle impossible to spatially reduce the excitation to the focal plane or to the focal volume. Similarly, it is also not possible to delimit the de-excitation to the focal plane. This means that molecules of the fluorescent dye above and below the focal plane are excited and may thus also be de-excited by the de-excitation light or even have to be de-excited. Although it is possible to reduce the measurement area along the optical axis to the focal plane by using a confocal pinhole in front of the detector, this still means that the fluorescent dye is unnecessarily excited and de-excited outside the focal plane which results in a considerable bleaching of the fluorescent dye particularly by the high intensity de-excitation light, and thus prevents capturing of 3D images with many fluorescent dyes.

As an option in fluorescence microscopy to delimit the imaging of a sample to the focal plane and to achieve a selectivity along the optical axis, it is known to excite the fluorescent dye with the excitation light via a multi photon process. In principle, the excitation light may have components of different wavelengths here, and three or even more single photons may be involved in the multi photon process. In the praxis of multi photon excitation of a fluorescent dye, however, only a two-photon excitation by excitation light of one wavelength is used, in which each photon contributes one half of the total photon energy required for the multi photon process. The selectivity of the excitation for the focal plane here relies on the non-linearity between the intensity of the excitation light and the excitation probability of the fluorescent dye into its fluorescent state via the multi photon process. In a two photon excitation this excitation probability depends on the square of the intensity of the excitation light, and thus concentrates to the diffraction main maximum of the focal range of the excitation light in the sample. To obtain a sufficient yield of fluorescent light from the sample in view of the generally lower transition probability of the fluorescent dye in the multi photon process, without subjecting the sample to extreme intensities of the excitation light, it is known to concentrate the excitation light temporally to single pulses. Due to this temporal concentration of the excitation light and the accompanying increased photon concentration in each single pulse of the excitation light, there is a considerably increased yield of fluorescent light as compared to excitation light which is continuously applied to the sample, i.e. at a temporally constant intensity. For example, the temporal concentration of the excitation light to a tenth of the time provides for an intensity of the excitation light increased by a factor of ten during this tenth of the time and thus for a yield of fluorescent light increased by a factor of $10^2=100$ during this tenth of the time. Averaged over the time, this still results in an increase of the intensity of the fluorescent light by 100/10=10 at the same mean intensity of the fluorescent light.

From DE 10 2005 027 896.5 A1 it is known in STED fluorescent light microscopy as well as in fluorescent light microscopy with multi photon excitation of the fluorescent dye to vary a temporal repetition distance of an optical signal applied to the sample in a range of at least 0.1 µs to 2 µs to maximize the fluorescent light yield. Here, the optical signal may come from a continuous wave laser, if a scanning device is provided for spatially scanning the sample with the optical signal which displays such a scanning speed that the desired repetition distance is adjusted. The intervals provided by the repetition distance allow the fluorescent dye to relax out of a dark state, particularly out of a triplet state, into which it gets at a certain fraction each time it is subjected to the optical signal, back into its fluorescent singlet state.

A method of high spatial resolution imaging a structure in a sample marked with a fluorescent dye and a system suitable to this end are known from WO 2007/030835 A2. Here, the fluorescent dye is a compound which has a dark state in which it is not excitable for fluorescence, and a fluorescent state in which it is excitable for fluorescence by excitation light. By means of switching-on light, the compound is switchable out of its dark state into the fluorescent state, wherein the transfer into the fluorescent state shall take place via an intermediate state out of which the compound shall be re-transferable back into the dark state with a pulse of switching-back light after a pulse of the switching-on light. By means of this switching-back light, the switched-on state is delimited to a measurement area which is reduced in size as compared to the focal area of the switching-on light. The actual measurement then takes place with excitation light that excites the compound in the fluorescent state for fluorescence. This excitation light may have the same wavelength as the switching-back light but has another spatial distribution and, in any case, simultaneously acts as switching-off light which switches the compound switched-on into its fluorescent state back into its dark state. A further pulse of the switching-on light with a following pulse of the switching-back light has to be applied to the sample to be able to go on measuring afterwards. The pulsed switching-on light may have such a wavelength that it switches the compound into its fluorescent state via a multi photon process. The excitation light which simultaneously acts as switching-off light may be provided by a continuous wave laser, like, for example, a diode laser, which may be switched on and off as required. De-excitation light which de-excites the compound excited for fluorescence prior to the spontaneous emission of fluorescent light is not used according to WO 2007/030835 A2. The efforts for the method and the system used for implementing the method known from this international patent application publication are high as light of at least three different wavelengths and/or spatial distributions, i.e. the switching-on light, the switching-back light and the excitation light also acting as switching-off light, has to be provided. Further, the switching-on light and the switching-back light have to be provided in exactly synchronized pulses as the intermediate state of the switchable compound onto which the switching-back light may act upon only has a short lifetime. Already the use of switchable fluorophores means a basic effort which goes far beyond the effort in using simple fluorescent dyes.

From U.S. Pat. No. 6,958,470 B2 it is known to provide the excitation light and the de-excitation light by two synchronized pulsed lasers at a repetition rate of about 800 MHz in STED fluorescent light microscopy.

There is still a need of a method and a system of three-dimensionally (3D) high spatial resolution imaging of a structure in a sample marked with a fluorescent dye, which may be realized with comparatively low effort, which avoid premature bleaching of the sample by de-excitation light, which nevertheless allows for a considerable increase in the spatial resolution beyond the diffraction barrier in all spatial directions.

SUMMARY OF THE INVENTION

In one aspect, the present invention provides a method of high spatial resolution imaging a structure of interest in a sample, the method comprising the steps of: marking the structure of interest with molecules of a fluorescent dye; selecting a first wavelength for excitation light which excites the molecules of the fluorescent dye via a multi photon process for spontaneous emission of fluorescent light; focussing pulses of the excitation light of the first wavelength into the sample to excite those molecules of the fluorescent dye which are present in at least one focal area of the focussed excitation light for the spontaneous emission of fluorescent light; selecting a second wavelength, which is shorter than the first wavelength, for de-excitation light which de-excites excited molecules of the fluorescent dye prior to their spontaneous emission of fluorescent light; during a plurality of the pulses of the excitation light, continuously directing a pattern of the de-excitation light of the second wavelength onto the sample to de-excite excited molecules of the fluorescent dye, which are located outside at least one measurement area which is a fraction of the at least one focal area; and recording the fluorescent light spontaneously emitted by the molecules of the fluorescent dye in the sample.

In a more detailed aspect, the present invention provides a method of high spatial resolution imaging a structure of interest in a sample, the method comprising the steps of: marking the structure of interest with molecules of a fluorescent dye; selecting a first wavelength for excitation light which excites the molecules of the fluorescent dye via a multi photon process for spontaneous emission of fluorescent light; focussing pulses of the excitation light of the first wavelength having a duration of at least 0.1% of their pulse distance and a frequency of at least 120 MHz into the sample to excite those molecules of the fluorescent dye which are present in at least one focal area of the focussed excitation light for the spontaneous emission of fluorescent light; selecting a second wavelength, which is shorter than the first wavelength, for de-excitation light which de-excites excited molecules of the fluorescent dye prior to their spontaneous emission of fluorescent light; during a plurality of the pulses of the excitation light, continuously directing a pattern of the de-excitation light of the second wavelength onto the sample to de-excite excited molecules of the fluorescent dye, which are located outside at least one measurement area which is a fraction of the at least one focal area, the pattern of the de-excitation light comprising bright areas located in front of and behind the measurement area with regard to the direction of an optical axis of the excitation light, and continuously recording the fluorescent light spontaneously emitted by the molecules of the fluorescent dye in the sample; and three-dimensionally scanning the sample with the at least one measurement area; wherein the steps of focussing and continuously directing are interrupted for a specific interruption period each time a predetermined number of the pulses of the excitation light has been focussed into the sample, the interruption period having a duration ranging between about 0.5 and 50 μs, and a pulsation period in which the predetermined number of the pulses of the excitation light is focussed into the sample has a duration ranging between about 100 ns and 50 μs.

In another aspect, the present invention provides a high spatial resolution imaging system comprising: a sample in which a structure of interest is marked with molecules of fluorescent dye; a pulsed excitation light source emitting pulses of excitation light at a first wavelength which excites the molecules of the fluorescent dye via a multi photon process; optics focussing the pulses of the excitation light of the first wavelength into the sample to excite those molecules of the fluorescent dye which are present in at least one focal area of the focussed excitation light for spontaneous emission of fluorescent light; a continuous wave de-excitation light source emitting de-excitation light at a second wavelength shorter than the first wavelength, which de-excites excited molecules of the fluorescent dye prior to their spontaneous emission of fluorescent light; optics continuously directing a pattern of the de-excitation light of the second wavelength onto the sample to de-excite excited molecules of the fluorescent dye, which are located outside at least one measurement area which is a fraction of the at least one focal area, during a plurality of the pulses of the excitation light; and a sensor recording the fluorescent light spontaneously emitted by the molecules of the fluorescent dye in the sample.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention will be better understood with reference to the following drawings. The components in the drawings are not necessarily to scale, emphasis instead being placed upon clearly illustrating the principles of the present invention.

DETAILED DESCRIPTION

Figure 1:
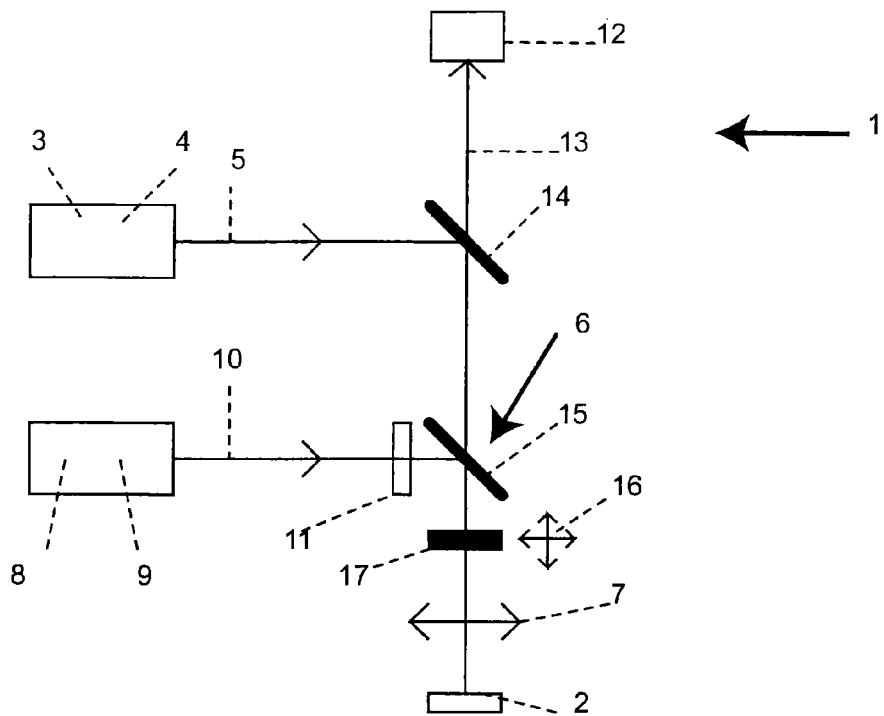
FIG. 1 schematically shows the configuration of an embodiment of the new system.

In the new method, the wavelength of the excitation light is selected in such a way that the excitation light excites the fluorescent dye via a multi photon process. Normally, this will be a two-photon process. Whereas the excitation light for the multi photon excitation is pulsed, which has a positive effect on the fluorescence light yield from the multi photon excitation, the de-excitation light which has a shorter wavelength than the excitation light is continuously directed onto the sample during a plurality of pulses of the excitation light. Because of the excitation of the fluorescent dye with the excitation light via a multi photon process, the focal area in which an effective excitation of the fluorescent dye takes place is considerably spatially limited as compared to an excitation via a single photon process. Particularly, with high aperture objectives, the non-linear excitation by the multi photon process is delimited to a focal depth of typically about ~1 μm which corresponds to the extension of a diffraction main maximum of an interference pattern of coherent light along the optical axis. Due to the fact that the excitation is spatially limited in three dimensions, fewer of even no molecules of the fluorescent dye which are located above or beneath the focal plane have to be de-excited. Particularly, molecules of the fluorescent dye which are outside the focal main maximum and which would otherwise be excited via a single photon process have not to be de-excited by the de-excitation light in the new method.

Preferably, the wavelength of the de-excitation light is selected in such a way that it falls within the red end range of the emission spectrum of the fluorescent dye. With de-excitation light from the red end of the emission spectrum of the fluorescent dye, bleaching by de-excitation light may only occur with already excited fluorescent dyes as its photon energy is too small to excite the fluorescent dye. In General, the de-excitation light may not only de-excite fluorescent dyes which have already been excited but also bleach them.

As the excitation via multi photon excitation is a priori three-dimensionally delimited to the diffraction main maximum, the area in which the molecules of the fluorescent dye have to be repeatedly de-excited is also strongly reduced in size. By reducing the number of the unnecessary de-excitations per molecule of the fluorescent dye the bleaching is also reduced, which makes nanoscale three-dimensional imaging via STED fluorescence microscopy considerably easier and even allows for it with many dyes for the first time. If the multi photon excitation only takes place in a 1 μm thick layer, the number of the unnecessary de-excitations in a 10 μm thick sample is reduced by a factor of 10. Further, as the area of the sample in which the de-excitation light is required to be strongly reduced in size as compared to the measurement area, the bleaching by the de-excitation light is also reduced correspondingly. The overall strong reduction of the bleaching of the fluorescent dye is basically achieved by exciting the fluorescent dye for fluorescence via a multi photon process.

Because of the foregoing, it is becomes possible to apply the de-excitation light to the sample in a continuous form, i.e. in a particularly cost saving way, without overstressing the fluorescent dye. Cost advantages in this context do not only occur due to doing without pulsing the de-excitation light, but also due to the avoided necessity to provide for a synchronization between the pulses of the excitation light and the pulses of the de-excitation light. Thus, executing the new method on a fluorescent light microscope which is already equipped for multi photon excitation of the fluorescent dye is only associated with minimum additional efforts. It is only required to provide the de-excitation light by means of a simple continuous wave laser, and to feed it into the objective of the fluorescent light microscope in a suitable way.

Any synchronization of the detector for the fluorescent light spontaneously emitted by the fluorescent dye with any pulses of the excitation or de-excitation light may also be completely avoided. Thus, the detector may continuously record the fluorescent light spontaneously emitted by the fluorescent dye over several pulses of the excitation light. Instead, the detector may extract the fluorescent light from the de-excitation light for example via an edge filter or a narrow-band bandpass filter or by means of a polarization filter, if the de-excitation light is suitably polarized.

It is particularly preferred in the new method, that the de-excitation light is provided by a diode laser. Such diode lasers may be provided at a tenth of the cost of a pulse laser which is commonly used for providing the de-excitation light in STED fluorescent light microscopy.

In the new method, in is noticed as a great advantage that the effective multi photon excitation of the sample by the excitation light is at any time also delimited to a smaller spatial area and that thus the overall load with excitation light which results in a danger of bleaching the fluorescent dye is also reduced as compared to the fluorescence yield.

In the new method, the excitation light may be pulsed at a comparatively high frequency of at least 80 MHz, preferably at least 100 MHz, more preferably at least 120 MHz and most preferably of at least 150 MHz. At least the two last figures exceed the usual frequency range of pulse lasers which are typically used in STED fluorescent light microscopy. This range is from 80 to 100 MHz. Due to the very high frequency of the pulses of the excitation light, the absolute intervals between the pulses of the excitation light are very short. Nevertheless, no parts of the de-excitation light are applied to the sample without very large parts of the fluorescent dye being in their excitable basic state. Thus no parts of the de-excitation light are wasted.

The single pulses of the excitation light are preferably comparatively short as compared to their pulse distance. Thus, the single pulses of the excitation light may have a duration of at maximum a tenth, preferably of at maximum a hundredth, more preferably of at maximum a thousandth, and most preferably of at maximum a tenthousandth of their pulse distance. As already explained at the beginning, the relative yield of fluorescent light from the sample is increased in this way with an unchanged mean intensity of the excitation light.

Particularly, it is possible in the new method to three-dimensionally scan the sample with the measurement area or a multitude of similar measurement areas from which the fluorescent light spontaneously emitted by the fluorescent dye is separately registered, wherein the structure in the sample marked with the fluorescent dye is three-dimensionally resolved at high spatial resolution.

To achieve this resolution particularly in z-direction, i.e. in the direction of the optical axis of the excitation light, it is preferred to direct the de-excitation light in front of and behind the measurement area onto the sample in this direction, like it is generally known from Proc. Natl. Acad. Sc. USA, 97, 8206 (2000). In the method of the present invention, one maximum on both sides of a null of an interference pattern of the de-excitation light intensity at the location of the measurement area is sufficient to de-excite the fluorescent dye which has been excited in the focal area of the excitation light for fluorescence by multi photon excitation. In general, several methods and apparatus for modifying the de-excitation beam are known which have the result that the focal measurement area is advantageously delimited: Phys. Rev. E, 64, 066613 (2001); Appl. Phys. B 77: 11 (2003); New J. Phys. 8: 106 (2006).

It is also advantageous to arrange a confocal pinhole, and in case of several measurement areas a confocal array of pinholes, in front of the detector. Pinholes reduce stray light both from the de-excitation light and from the excitation light. In a further specific embodiment the fluorescent light is not guided back via the optical scanning device but via a simplified optical path, i.e. with a "non-descanned detection" as it is generally known to those skilled in the art.

In a specific embodiment of the new method, the excitation might and the de-excitation light are interrupted each time a predetermined number of the pulses of the excitation light have been focussed into the sample. These interruptions have the purpose of waiting for the relaxation of the fluorescent dye out of a dark state, particularly its triplet state, back into the fluorescent singlet state, after this dark state has been populated during the previous pulses of the excitation light to a considerable extent. The population of the dark state results in a reduced yield of fluorescent light from the sample and may also be associated with an increased danger of bleaching the fluorescent dye. The dark state, however, decays or relaxes over a comparatively short period in a range of 0.5 to 3 µs, typically 1 to 2 µs, so that a corresponding interruption of the excitation results in an overall increased yield of fluorescence light from the sample. Suitably, the de-excitation light is also interrupted for the interruption periods mentioned in parallel to the supply of the excitation light to not unnecessarily subject the sample to the de-excitation light. The pulsation periods within which the predetermined number of the pulses of the excitation light is focussed into the sample and the de-excitation light is continuously applied to the sample vice versa typically range from 100 ns to 50 µs and preferably from 0.5 to 2 µs. The exact duration of these pulsation periods depend on how quickly the triplet state or the dark state is populated in practice.

In a high spatial resolution imaging system according to the present invention the excitation light source emits the excitation light at such a wavelength that the excitation light excites the fluorescent dye via a multi photon process, and the de-excitation light source directs the de-excitation light which has a shorter wavelength than the excitation light continuously onto the sample during a plurality of pulses of the excitation light.

The detector of the new system may also continuously record the fluorescent light spontaneously emitted by the fluorescent dye during several pulses of the excitation light.

The realization of the new system is particularly convenient, if the de-excitation light source comprises a continuously emitting diode laser. The excitation light source, however, comprises a pulse laser which emits the excitation light in pulses at the above mentioned high frequency and short relative duration with regard to their distance. A scanning device which may be provided in the new system to three-dimensionally scan the sample with the measurement area or a multitude of similar measurement areas, from which the detector separately registers the fluorescent light spontaneously emitted by the fluorescent dye, may generally move the sample with regard to the remainder of the fluorescent light microscope. Preferably, however, scanning is effected by moving an optical element which both belongs to the optics focussing the excitation light into the sample and to the optics directing the de-excitation light onto the sample. Various devices for scanning a focussed beam over the sample are sufficiently known to those skilled in the art from the literature of laser scanning microscopy.

To the end of interrupting the excitation light and the de-excitation light incident on the sample for a specific interruption period each time a predetermined number of the pulses of the excitation light have been focussed into the sample, the new system may comprise a control device which is preferably adjustable to adjust the specific interruption period as well as the pulsation period of number of pulses which extends between two such interruption periods. Such a control device preferably includes acousto-optical or electro-optical beam modulators. The detector of the new system does by the way not need to be synchronized with the interruption periods in which the excitation light and the de-excitation light are interrupted but may continuously record the fluorescent light spontaneously emitted by the fluorescent dye even during these interruption periods as there is no fluorescent light during these interruption periods.

Referring now in greater detail to the drawings, an apparatus 1 sketched in FIG. 1 serves for high spatial resolution imaging a structure in a sample 2 which has been marked with a fluorescent dye. To this end, pulsed excitation light 5 is directed through optics 6 into a focal area of an objective 7 in the sample by means of an excitation light source 3 which is a pulse laser 4. Within this focal range, the fluorescent dye in the sample 2 is excited for fluorescence, i.e. for spontaneous emission of fluorescent light, via a two-photon process. The focal area is here defined as that area in which an effective excitation of the fluorescent dye for spontaneous emission of fluorescent light via the two photon process occurs due to the excitation light 5. In a partial area of the focal area, i.e. outside a measurement area which is reduced in size as compared to the focal area, the fluorescent dye is instantaneously de-excited in that de-excitation light 10 is continuously directed onto the sample by means of a de-excitation light source 8 which is a diode laser 9. Plane wave fronts of the de-excitation light 10 emitted by the de-excitation light source 8 are deformed by means of a phase modulator 11 in such a way that an intensity distribution of the de-excitation light 10 with a central null and adjacent intensity maxima covering the remainder of the focal area is built up in the focal area. Thus, a detector 12 which records fluorescent light spontaneously emitted by the fluorescent dye in the sample 2 only senses fluorescent light which originates from the measurement area having dimensions below the diffraction barrier at the wavelength of the light used. The excitation light 5 is kept away from the detector 12 by means of a dichroitic mirror 14 which separates the beam paths of the excitation light 5 and of the fluorescent light 13. The de-excitation light 10 is kept away from the detector 12 by a further dichroitic mirror 15 which separates the beam paths of the de-excitation light 10 and of the fluorescent light 13. A scanning device 16 may be provided for moving an optical element 17 of the optics 6, through which both the excitation light 5 and the de-excitation light 10 as well as the fluorescent light 13 from the sample pass, in such a way that those structures marked with the fluorescent dye in the sample are three-dimensionally scanned.

Figure 2:
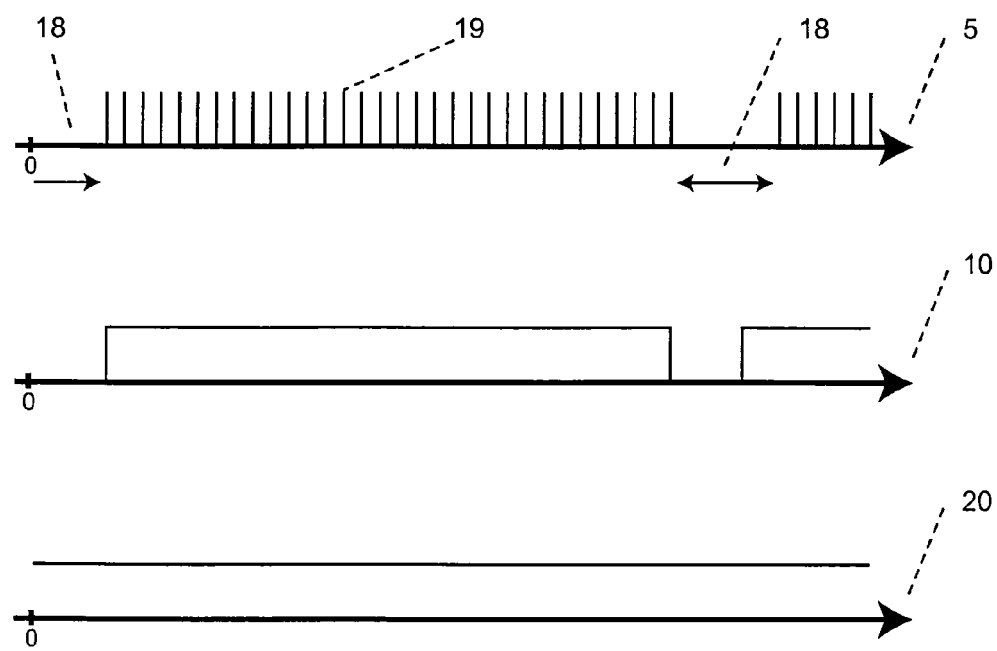
FIG. 2 schematically shows the time course of the intensity of the excitation light on top, the time course of the intensity of the de-excitation light in the middle, and the time course of the sensitivity of the detector for recording fluorescent light from a sample at the bottom, in an embodiment of the new method.

FIG. 2 shows the temporal course of the intensity of the excitation light 5 on top. Between specific interruption periods 18 in which the intensity of the excitation light is zero, the excitation light consists of single pulses with a pulse duration shorter than their distance. The specific periods 18 have a typical duration of 1 µs. The frequency of the pulses 19 of the excitation light 5 is above 120 MHz, wherein their distance is at least ten times longer than their duration. These ratios are not completely reflected in FIG. 2. In the middle, FIG. 2 shows the temporal intensity course of the de-excitation light 10. The de-excitation light 10 is continuously, i.e. at constant intensity, applied to the sample 2, except for the interruption periods 18 in which its intensity is also zero. On the bottom, FIG. 2 shows the temporal course of the sensitivity 20 of the detector 12 according to FIG. 1. The sensitivity is constant, i.e. it is also present during the periods 18.

Many variations and modifications may be made to the preferred embodiments of the invention without departing substantially from the spirit and principles of the invention. All such modifications and variations are intended to be included herein within the scope of the present invention, as defined by the following claims.

LIST OF REFERENCE NUMERALS 1 apparatus
2 sample
3 excitation light source
4 pulse laser
5 excitation light
6 optics
7 objective
8 de-excitation light source
9 diode laser
10 de-excitation light
11 phase modulator
12 detector
13 spontaneously emitted fluorescent light
14 dichroitic mirror
15 dichroitic mirror
16 scanning device
17 optical element
18 interruption period
19 pulse
20 sensitivity

We claim:

1. A method of high spatial resolution imaging a structure of interest in a sample, the method comprising the steps of:
    marking the structure of interest with molecules of a fluorescent dye;
    selecting a first wavelength for excitation light which excites the molecules of the fluorescent dye via a multi photon process for spontaneous emission of fluorescent light;
    focussing pulses of the excitation light of the first wavelength into the sample to excite those molecules of the fluorescent dye which are present in at least one focal area of the focussed excitation light for the spontaneous emission of fluorescent light;
    selecting a second wavelength, which is shorter than the first wavelength, for de-excitation light which de-excites excited molecules of the fluorescent dye prior to their spontaneous emission of fluorescent light;
    during a plurality of the pulses of the excitation light, continuously directing a pattern of the de-excitation light of the second wavelength onto the sample to de-excite excited molecules of the fluorescent dye, which are located outside at least one measurement area which is a fraction of the at least one focal area; and
    recording the fluorescent light spontaneously emitted by the molecules of the fluorescent dye in the sample.

2. The method of claim 1, wherein the step of recording includes continuously recording the fluorescent light spontaneously emitted by the molecules of the fluorescent dye in the sample while several pulses of the excitation light are focussed into the sample in the step of focussing.

3. The method of claim 1, wherein the step of continuously directing includes providing the de-excitation light with a diode laser.

4. The method of claim 1, wherein the step of focussing includes pulsing the excitation light at a frequency of at least 80 MHz.

5. The method of claim 4, wherein the step of focussing includes pulsing the excitation light at a frequency of at least 100 MHz.

6. The method of claim 5, wherein the step of focussing includes pulsing the excitation light at a frequency of at least 120 MHz.

7. The method of claim 6, wherein the step of focussing includes pulsing the excitation light at a frequency of at least 150 MHZ.

8. The method of claim 1, wherein the step of focussing includes pulsing the excitation light in such a way that the individual pulses of the excitation light have a duration of at least 1% of their pulse distance.

9. The method of claim 8, wherein the step of focussing includes pulsing the excitation light in such a way that the individual pulses of the excitation light have a duration of at least 1% of their pulse distance.

10. The method of claim 9, wherein the step of focussing includes pulsing the excitation light in such a way that the individual pulses of the excitation light have a duration of at least 0.1% of their pulse distance.

11. The method of claim 10, wherein the step of focussing includes pulsing the excitation light in such a way that the individual pulses of the excitation light have a duration of at least 0.001% of their pulse distance.

12. The method of claim 1 and further comprising the step of three-dimensionally scanning the sample with the at least one measurement area.

13. The method of claim 1 and further comprising the step of three-dimensionally scanning the sample with a plurality of measurement areas, wherein in the step of recording the fluorescent light spontaneously emitted by the molecules of the fluorescent dye in the individual measurement areas is recorded separately.

14. The method of claim 1, wherein in the step of continuously directing the pattern of the de-excitation light is an interference pattern comprising bright areas located in front of and behind the measurement area as viewed in the direction of an optical axis of the excitation light.

15. The method of claim 1, wherein the steps of focussing and continuously directing are interrupted for a specific interruption period each time a predetermined number of the pulses of the excitation light have been focussed into the sample.

16. The method of claim 15, wherein the interruption period has a duration ranging between about 0.5 and 50 μs.

17. The method of claim 16, wherein the interruption period has a duration ranging between about 1 and 2 μs.

18. The method of claim 15, wherein a pulsation period in which the predetermined number of the pulses of the excitation light is focussed into the sample has a duration ranging between about 100 ns and 50 μs.

19. The method of claim 18, wherein the pulsation period has a duration ranging between about, preferably 0.5 and 2 μs.

20. A method of high spatial resolution imaging a structure of interest in a sample, the method comprising the steps of:
marking the structure of interest with molecules of a fluorescent dye;
selecting a first wavelength for excitation light which excites the molecules of the fluorescent dye via a multi photon process for spontaneous emission of fluorescent light;
focussing pulses of the excitation light of the first wavelength having a duration of at least 0.1% of their pulse distance and a frequency of at least 120 MHz into the sample to excite those molecules of the fluorescent dye which are present in at least one focal area of the focussed excitation light for the spontaneous emission of fluorescent light;
selecting a second wavelength, which is shorter than the first wavelength, for de-excitation light which de-excites excited molecules of the fluorescent dye prior to their spontaneous emission of fluorescent light;
during a plurality of the pulses of the excitation light,
continuously directing a pattern of the de-excitation light of the second wavelength onto the sample to de-excite excited molecules of the fluorescent dye, which are located outside at least one measurement area which is a fraction of the at least one focal area, the pattern of the de-excitation light comprising bright areas located in front of and behind the measurement area with regard to the direction of an optical axis of the excitation light; and
continuously recording the fluorescent light spontaneously emitted by the molecules of the fluorescent dye in the sample; and
three-dimensionally scanning the sample with the at least one measurement area;
wherein the steps of focussing and continuously directing are interrupted for a specific interruption period each time a predetermined number of the pulses of the excitation light has been focussed into the sample, the interruption period having a duration ranging between about 0.5 and 50 μs, and a pulsation period in which the predetermined number of the pulses of the excitation light is focussed into the sample has a duration ranging between about 100 ns and 50 μs.

21. A high spatial resolution imaging system comprising:
a sample in which a structure of interest is marked with molecules of fluorescent dye;
a pulsed excitation light source emitting pulses of excitation light at a first wavelength which excites the molecules of the fluorescent dye via a multi photon process;
optics focussing the pulses of the excitation light of the first wavelength into the sample to excite those molecules of the fluorescent dye which are present in at least one focal area of the focussed excitation light for spontaneous emission of fluorescent light;
a continuous wave de-excitation light source emitting de-excitation light at a second wavelength shorter than the first wavelength, which de-excites excited molecules of the fluorescent dye prior to their spontaneous emission of fluorescent light;
optics continuously directing a pattern of the de-excitation light of the second wavelength onto the sample to de-excite excited molecules of the fluorescent dye, which are located outside at least one measurement area which is a fraction of the at least one focal area, during a plurality of the pulses of the excitation light; and
a sensor recording the fluorescent light spontaneously emitted by the molecules of the fluorescent dye in the sample.

22. The system of claim 21, wherein the detector continuously records the fluorescent light spontaneously emitted by the fluorescent dye while several pulses of the excitation light are emitted by the excitation light source.

23. The system of claim 21, wherein the de-excitation light source comprises a diode laser for emitting the de-excitation light.

24. The system of claim 21, wherein the excitation light source comprises a pulse which emits the pulses of the excitation light at a frequency of at least 100 MHz and at a duration of at maximum a hundredth of their distance.

25. The system of claim 21 and further comprising a scanning device three-dimensionally scanning the sample with the at least one measurement area.

26. The system of claim 21 and further comprising a scanning device three-dimensionally scanning the sample with a plurality of measurement areas, wherein the sensor separately records the fluorescent light spontaneously emitted by the molecules of the fluorescent dye in the individual measurement areas.

27. The system of claim 21, wherein the optics directing the de-excitation light onto the sample modify plane wave fronts of the de-excitation light in such a way that the de-excitation light has intensity maxima in front of and behind the measurement area in the direction of an optical axis of the excitation light.

28. The system of claim 21 and further comprising a control device interrupting emission of the excitation light by the excitation light source and the emission of the de-excitation light by the de-excitation light source for a specific interruption period each time a predetermined number of the pulses of the excitation light have been emitted by the excitation light source.

29. The system of claim 28, wherein the specific interruption period is adjustable at least in a range from about 1 to 2 µs.

30. The system of claim 28, wherein a pulsation period of the predetermined number of pulses of the excitation light is adjustable at least in a range from about 0.5 ns to 2 µs.

* * * * *